United States Patent [19]

Grundman

[11] 3,991,174

[45] Nov. 9, 1976

[54] METHOD OF DETERMINING CONCENTRATION OF LUTEINIZING HORMONE IN BODY FLUID

[75] Inventor: Lea Grundman, Jerusalem, Israel

[73] Assignee: Rafa Laboratories Ltd., Israel

[22] Filed: Apr. 17, 1975

[21] Appl. No.: 568,857

Related U.S. Application Data

[63] Continuation-in-part of Ser. No. 202,004, Nov. 24, 1971, abandoned, which is a continuation-in-part of Ser. No. 125,428, March 17, 1971, abandoned.

[30] Foreign Application Priority Data

July 20, 1970  Israel...................................... 34960
Apr. 21, 1974  Israel...................................... 44675

[52] U.S. Cl.................................. 424/12; 424/100; 424/105
[51] Int. Cl.$^2$.................. A61K 39/00; G01N 31/00; G01N 33/16
[58] Field of Search.................. 424/8, 12, 99, 100, 424/105

[56] References Cited
UNITED STATES PATENTS 3,553,310   1/1971   Csizmas............................... 424/12
3,565,987   2/1971   Schuurs................................ 424/12

OTHER PUBLICATIONS

Schuurs, Acta Endocrinnol. Suppl., 1969, No. 142, pp. 95–112.

Echt, Chem. Abs., vol. 66, 1967, No. 52591a.

Chem. Abs., vol. 72, 1970, Nos. 51320y, 51321z, 51322a, 51324c.

Reiss, Chem. Abs., vol. 67, 1967, No. 9790y.

*Primary Examiner*—James O. Thomas, Jr.
*Assistant Examiner*—A. P. Fagelson
*Attorney, Agent, or Firm*—Steinberg & Blake

[57] ABSTRACT

The invention relates to a method of determining the concentration of luteinizing hormone (hereinafter referred to as "LH") in the body fluid of a woman and thereby determining the day when said woman ovulates, as well as to compositions for effecting this determination. The composition comprises human chorionic gonadotropin (hereinafter referred to as "HCG") coupled to red blood cells by means of glutaraldehyde as coupling agent therebetween, which composition in carrying out the test is mixed with the body fluid of the woman and an anti-HCG serum in an amount adjusted to react with approximately 50 international units (I.U.) of HCG per liter of the body fluid, generally urine, so that agglutination occurs when LH equivalent to less than 50 I.U. of HCG/L is present and no agglutination when at least 50 I.U. HCG/L is present. The day of highest concentration of LH equivalent to HCG indicating the day of ovulation.

6 Claims, 1 Drawing Figure

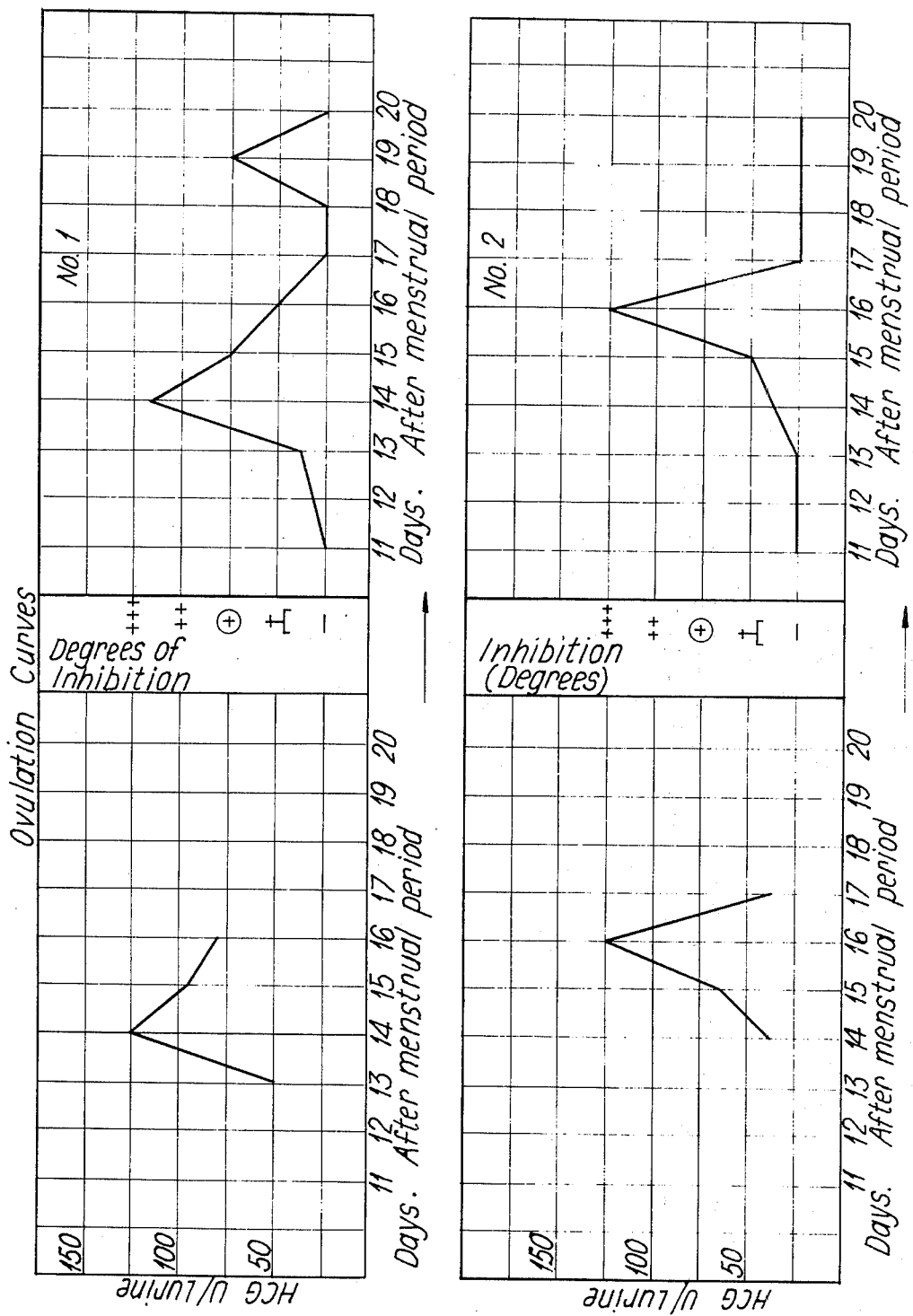

METHOD OF DETERMINING CONCENTRATION OF LUTEINIZING HORMONE IN BODY FLUID

CROSS REFERENCE TO RELATED APPLICATIONS

This application is a continuation-in-part of my copending application Ser. No. 202,004, filed Nov. 24, 1971, now abandoned, for "Pregnancy Determining Composition and Method," which in turn is a continuation-in-part of my copending application Ser. No. 125,428, filed Mar. 17, 1971, for "A Method for the Determination of Pregnancy and Serodiagnostic Composition Therefor," now abandoned.

BACKGROUND OF THE INVENTION

During ovulation increased concentrations of LH are found in the body fluid of the woman. Before ovulation the concentration of the LH in urine is about 25 –100 I.U./Liter which rises to a peak of about 150 –600 I.U./Liter at the time of ovulation. By testing urine samples daily between two menstrual periods it is possible to determine the day on which the LH concentration rises to its peak and thus, the day of ovulation, i.e. the day on which the woman is fertile.

It has been found that the concentration of the LH can be estimated by means of an immunoassay using HCG as standard because the two hormones cross-react serologically. Thus, one I.U. of HCG = 2.5 I.U. of LH. The present invention makes use of this cross-reactivity. Erythrocytes sensitized with HCG are agglutinated with an anti-HCG serum. The hemagglutination is inhibited in the presence of free HCG beginning with a predetermined concentration thereof in the body fluid or in the presence of an equivalent concentration of LH.

This predetermined concentration is a function of the sensitivity of the test. The sensitivity can be adjusted to any desired value by altering the concentration of the reactant. It has been found that, for the purpose of the present invention, by adjusting the reactants so that hemagglutination is inhibited starting with a concentration of LH equivalent to 50 I.U./Liter of free HCG in the body fluid, it is possible to determine the day of ovulation, which is the day on which the woman is most fertile.

SUMMARY OF THE INVENTION

In accordance with the present invention the day on which a woman ovulates is determined by the daily testing of samples of the woman's body fluid, urine being preferred, by means of a composition consisting essentially of HCG coupled to red blood cells by means of glutaraldehyde as coupling agent, utilizing anti-HCG, by taking advantage of the cross-reactivity of HCG and LH in order to determine the day on which the concentration of LH in the urine is at its peak, which is the day of ovulation.

It is accordingly a primary object of the present invention to provide for a method of accurately determining the day on which a woman ovulates.

It is another object of the present invention to provide a method of determining the day of ovulation between menstrual periods for thus determining the day of greatest fertility of the woman by testing a woman's urine for the concentration of LH therein by utilizing a composition of HCG coupled to red blood cells by means of glutaraldehyde as coupling agent therebetween.

Other objects and advantages of the present invention will be apparent from a further reading of the specification and of the appended claims.

With the above and other objects in view, the present invention mainly comprises a method for determining the concentration of LH in the body fluid of a woman by reacting the urine with HCG coupled to red blood cells by means of glutaraldehyde and with anti-HCG in an amount such that up to 50 I.U., equivalent to HCG, per liter of LH will react with anti-HCG, whereby hemagglutination occurs at less than 50 I.U., equivalent to HCG, if LH is present and no hemagglutination occurs if more than 50 I.U. per liter is present, the day of maximum concentration of LH in the urine being the day of ovulation.

The composition of HCG coupled to red blood cells by means of glutaraldehyde as coupling agent therebetween which is utilized in the determination of the concentration of LH in the woman's urine in accordance with the present invention is the same as and is prepared in the same manner as set forth in my copending U.S. patent application Ser. No. 202,004, filed Nov. 24, 1974, for "Pregnancy Determining Composition and Method." This composition of HCG coupled to red blood cells by means of glutaraldehyde may sometimes hereinafter be referred to as sensitized cells.

The red blood cells utilized for the purpose are preferably obtained from sheep, although the same may be obtained from any other animal such as mice or even from human beings. Particularly good results are obtained with respect to reduction in the time required for the test determination by the use of avian blood, particularly blood from fowl, and most particularly by the use of turkey blood.

The sensitized cells composition may be washed with a borate saline solution and then stored for a relatively long period of time. This storage time may be increased by the addition of gelatin, which may be added in amounts of up to about 1% weight/volume, preferably about 0.05–0.2%, and most preferably about 0.1%.

In order to further increase the stability of the serodiagnostic composition according to the present invention the sensitized blood cells may, after having been washed with borate saline solution, be further treated with glutaraldehyde or with formaldehyde.

If the method is carried out utilizing the known composition for the determination of LH, which is commercially sold under the name of "Luteonosticon," the carrying out of the test provides many serious drawbacks, including the following:

1. It is necessary to use centrifuged urine.
2. The diluent must be diluted.
3. The time of pre-incubation is about 2–4 hours.
4. A further incubation is required.
5. Centrifugation is necessary.
6. The pre-incubated mixture must be transferred to a second tube so that for each test at least two tubes are required.

When carrying out the test in accordance with the present invention utilizing the composition thereof, the above drawbacks are substantially overcome, namely:

1. It is not necessary to centrifuge the urine.
2. There is no need to dilute the diluent.

3. Only about 1 hour is required for preincubation.
4. No further incubation is required.
5. Centrifugation is not necessary.
6. The entire test can be carried out in a single tube.

In accordance with the method of the present invention the determination of concentration of LH in the body fluid of the woman who is being tested comprises admixing the body fluid with anti-HCG serum and mixing the thus obtained mixture with the above serodiagnostic composition. It is advantageous to permit the mixture of the body fluid and the anti-HCG serum to stand for about 1 hour before the addition of the serodiagnostic composition.

Serum or urine may be utilized as the body fluid. Most preferably freshly filtered morning urine is utilized.

At the beginning and at the end of the menstrual cycle, the concentration of LH in the urine is low, that is below that which is fixed for the sensitivity of the test. As a result, hemagglutination occurs. When the predetermined concentration is obtained, which is about 11 days in the case where the predetermined concentration is set at 50 I.U. HCG/liter of urine, no further hemagglutination occurs and a button or ring formation is observed. This occurs up to about the 20th day after the beginning of the cycle.

Any one experienced in carrying out the test can, depending upon the strength of the ring determine qualitatively the concentration of LH. However, this concentration can be determined quantitatively by diluting the urine and repeating the test. The day on which the concentration of the LH in the urine is the highest indicates the day of ovulation, that is the day on which the woman is fertile. By repeating the test for several months it is possible to ascertain on which day of the cycle the woman is fertile. This determination of the day on which the woman is fertile is one of the aspects of the present invention.

In accordance with the preferred embodiment of the present invention the method is carried out in a solution which is advantageously buffered at a pH of 5 - 8.5. However, this is not necessary for carrying out the invention. Thus, the serodiagnostic composition may be pressed into the form of a tablet, may be impregnated on a paper strip or the like. In any case the composition is then in suitable manner contacted with the mixture of the anti-HCG serum and the body fluid of the woman.

The components of the serodiagnostic composition must be selected in amounts such that the HCG is properly connected to the coated red cells. It is undesirable to utilize a large excess of any of the components of the composition.

It is also possible in accordance with the present invention to lyophilize the sensitized cells and the anti-HCG in which case the same can be mixed together and stored in this form. When this lyophilized form of the composition is utilized the test is carried out by simply mixing the same with the urine.

In carrying out the method of the present invention any known anti-HCG serum may be utilized so long as the same is sufficiently specific for the HCG. However, it is advantageous to utilize an anti-HCG serum prepared by the below indicated method. The amount of anti-HCG serum to be utilized is ascertained for each serum as shown below.

BRIEF DESCRIPTION OF THE DRAWING

The drawing in this case constitutes graphs comparing the results obtained comparing the observable degree of hemagglutination in accordance with the present invention with quantitative determination of the amount of luteinizing hormone in the urine.

No. 1 graphically compares the tests on one woman and No. 2 graphically compares the tests on another woman.

The graph on the right side for each test sets forth the results obtained by the observable degree of hemagglutination in accordance with the method of the present invention, and the corresponding graph on the left side for each woman sets forth the results obtained by quantitative determination of the amount of luteinizing hormone in the woman's urine for the day indicated.

DESCRIPTION OF PREFERRED EMBODIMENTS

The following Examples are given to further illustrate the present invention. The scope of the invention is not, however, meant to be limited to the specific details of the examples.

EXAMPLE 1

Preparation of absorbed anti-HCG serum a. 5 mg of a HCG preparation having a potency of 2500–3500 I.U./mg were dissolved in 5 ml of a 0.15 M phosphate buffer of pH 7.2. The solution obtained was homogenized with an equal volume of complete Freund's adjuvant.

| The phosphate buffer comprised: | |
|---|---|
| $NaH_2PO_4$ 0.15 M solution | 56 ml |
| $Na_2HPO_4$ 0.15 M solution | 147.5 ml |

The above potency of the HCG preparation is by no means critical for the success of the immunization procedure. The same applies to all following Examples.

It is readily understood that another buffer solution may be utilized as long as it fulfills the requirements. The pH range may be varied between about 5 to 8.5.

b. 0.1 ml and 0.5 ml of the above homogenate were injected into the foot pad of a rabbit weighing 2.5–3.0 kg and subcutaneously, respectively, once a week for 3 consecutive weeks.

c. One week after the last set of injections, the rabbit was bled and the serum was separated by centrifugation and stored in a refrigerator.

d. Unspecific antibodies were absorbed from the serum by mixing equal volumes of the serum and of normal human serum (not containing HCG, inactivated at 56° C for 30 minutes and absorbed on an equal volume of packed washed sheep red blood cells.) The mixture obtained is called "absorbed anti-HCG serum."

EXAMPLE 2

Preparation of highly specific absorbed anti-HCG serum a. A homogenate was prepared in the same manner as described in step (a) of Example 1.

b. 0.1 ml and 0.5 ml of the homogenate obtained in step (a) were injected into the foot pad and subcutaneously, respectively, of a rabbit weighing 2.5–3.0 kg, once a month for 3 consecutive months.

c. One week after the last set of injections, the rabbit was bled and the serum was separated by centrifugation and stored in a refrigerator.

d. Unspecific antibodies were absorbed from the serum in the same manner as described in step (d) of Example 1.

e. Further unspecific antibodies were absorbed by mixing the "absorbed anti-HCG serum" with 20–50% non-specific urinary proteins and removing the same after incubation. The serum obtained is called "highly specific absorbed anti-HCG serum".

The anti-HCG serum prepared either in Example 1 or in Example 2 was diluted with 0.15 M of phosphate-borate-saline (P.B.S.) to a suitable concentration and finally lyophylized.

| The P.B.S. solution comprised: | |
|---|---|
| $NaH_2PO_4$ 0.15 M solution | 33.2 ml |
| $Na_2HPO_4$ 0.15 M solution | 60.8 ml |
| NaCl | 8.5 g |
| Distilled water | 900.0 ml |

EXAMPLE 3

Preparation of the serodiagnostic composition 1 ml of a 2.5% glutaraldehyde solution in a phosphate buffer of pH 7.2 was added under constant stirring to the following mixture:

| | |
|---|---|
| 0.15 — M-0.5 M phosphate buffer pH 7.2 | 10 ml |
| packed sheep red blood cells | 0.4 ml |
| HCG, having the same potency as in Example 1, in a phosphate buffer of pH 2 having a concentration of 12 mg/ml | 0.5 ml |

Stirring was continued for 1 hour. The preparation was then washed 3 times with a borate saline solution (prepared as described hereinafter) and then stored in the refrigerator. Gelatin may be added to the suspension of sensitized cells, preferably in an amount of about 0.1% (W/V) for increased storability.

The method of preparation may be varied to a large extent. Thus, the pH of the buffer may vary between 5–8.5, the HCG solution may have a concentration of 4–12 mg/ml and the glutaraldehyde a concentration of 1–5%. In this respect reference is also made to Example 3 of Serial No. 202,004.

The borate solution was prepared as follows:

| a. | Sodium Chloride | 0.85% |
|---|---|---|
| b. | $H_3BO_3$ | 12.37 g |
| | NaOH | 0.52 g |
| | NaCl | 8.00 g |
| | $H_2O$ up to | 1000.00 ml |

Each 97 ml of a. were admixed with 3 ml of (b).
Sodium azide was added to a final concentration of 0.1%.

EXAMPLE 4

Standardization of anti-HCG serum

Twofold dilutions (in borate saline) of anti-HCG serum were prepared in suitable test tubes, each tube having a volume of 0.1 ml. 0.1 ml of the serodiagnostic composition, prepared as described in Example 3, were added to each test tube. The concentration of the red blood cells was 0.8%. The tubes were shaken and left to stand at room temperature for about 2 hours. At the end of this period, the results were read and the concentration of the highest dilution of the serum which still agglutinated in the red cells was determined. This concentration is the end point of the titration and is defined as "one hemagglutination unit". (h.u.). For the ovulation test according to the present invention a suitable concentration is used, which may vary from 1.0–8. h.u. and is preferably about 1.6 h.u.

EXAMPLE 5

Performance of the ovulation test a. Morning urine samples were collected from women each day of their menstrual cycle.

b. The lyophilized anti-HCG serum was dissolved by adding 0.5 ml of borate saline.

c. Aliquots of 0.1 ml of the anti-HCG serum solution were distributed into test tubes, which were marked according to the number of days after the last menstruation from which the urine samples were taken; and into 1 control tube.

d. 0.2 ml of filtered morning urine was added to its respective test tube.

e. 0.2 ml of borate saline solution was added to the control tube containing 0.1 ml of anti-HCG serum and 0.3 ml of borate saline solution was added to a second, empty, test tube.

f. The rack containing the test tubes was shaken lightly and left to stand for 1 hour without the influence of outside heat, e.g. heating, radiation, etc.

g. After 1 hour, 0.1 ml of the sensitized cells 0.8%, prepared as described in Example 3, was added to the respective tube and to each of the control tubes.

h. The rack containing the test tubes was shaken for 1 minute and then left to stand for 2 hours without vibration and without the influence of outside heat.

i. Finally it was observed whether there was hemagglutination or button or ring formation.

The distribution of the reagents was performed as shown in the following Table.

Table

| | DAYS BETWEEN TWO MENSTRUAL PERIODS | | | | | | | | | | | Serum Control | Erthrocyte Control |
|---|---|---|---|---|---|---|---|---|---|---|---|---|---|
| | 8 | 9 | 10 | 11 | 12 | 13 | 14 | 15 | 16 | 17 | 18 | | |
| anti-HCG (ml) | 0.1 | 0.1 | 0.1 | 0.1 | 0.1 | 0.1 | 0.1 | 0.1 | 0.1 | 0.1 | 0.1 | 0.1 | |
| Urine to be tested (ml) | 0.2 | 0.2 | 0.2 | 0.2 | 0.2 | 0.2 | 0.2 | 0.2 | 0.2 | 0.2 | 0.2 | | |
| Diluent (ml) | | | | | | | | | | | | 0.2 | 0.3 |

Evaluation of the Results

Hemagglutination resembling that observed in the serum control tube indicates that the respective test tube contains less than 50 I.U. HCG/1 urine.

A button or ring formation (similar to that observed in the erythrocyte control tube) indicates that the tested urine contains at least 50 I.U. HCG/1 urine, or more.

The quantity of the hormone rises gradually during the first days after menstruation from levels of 10–40 I.U. HCG (=25–100 I.U. LH)/1 urine, attains the maximum level of 60–240 I.U. HCG (=150–600 I.U. LH)/1 urine and decreases to the initial levels prior to the next menstruation.

In case that in more than one test tube levels of more than 50 I.U. HCG/L urine are observed, a quantitative test is advantageously performed so that the day of ovulation can be more precisely determined. The test is performed by diluting the urine.

The sensitivity of the test can be increased to 25 I.U. HCG/L urine by adding 0.4 ml of urine to a test tube containing 0.1 ml of anti-HCG serum (instead of 0.2 ml as used above) and by adding 0.2 ml of additional diluent to each of the control test tubes.

The results of the above tests carried out on two women during the middle period of the menstrual cycle are graphically illustrated in the graphs constituting the accompanying drawing. The qualitative results obtained by comparison of the observable degree of hemagglutination in accordance with the method of the present invention are set forth in the curves of the graphs on the right side for each woman with the corresponding quantitative measurement of the amount of luteinizing hormone in the woman's urine being set forth in the corresponding graph on the left side. It is apparent from the graph on the right side for woman No. 1 that her day of ovulation is the 14th day after menstruation. This is confirmed by the left side graph which shows a maximum content of luteinizing hormone for the same woman on her 14th day after menstruation. In the case of woman No. 2 it is apparent that her day of ovulation is the 16th day after menstruation by the test according to the present invention in the right hand graph of woman No. 2 and this is confirmed by the quantitative determination as set forth in the graph on the left hand side.

While the invention has been illustrated in particular with respect to the determination of the day of ovulation of a woman by testing of her urine, it is apparent that variations and modifications of the invention can be made.

What is claimed is:

1. Method for determining the concentration of luteinizing hormone in the body fluid of a woman, which comprises reacting the body fluid of the woman with a predetermined amount of anti-human chorionic gonadotropin and with a composition of human chorionic gonadotropin coupled to red blood cells by means of glutaraldehyde and also containing a stabilizing effective amount of gelatin, whereby hemagglutination occurs when said body fluid contains an amount of luteinizing hormone less than the amount which will react with all of said anti-human chorionic gonadotropin and no hemagglutination occurs when the amount of said luteinizing hormone in said body fluid is greater than the amount which will react with all of said predetermined amount of anti-human chorionic gonadotropin.

2. The method of claim 1 wherein said body fluid is urine.

3. The method of claim 2 wherein daily samples of filtered urine from said woman are mixed with predetermined amounts of anti-human chorionic gonadotropin and permitted to stand for about one hour, after which predetermined amounts of said human chorionic gonadotropin coupled to red blood cells by means of glutaraldehyde are added to said mixture which are then permitted to stand and the samples are examined to determine the relative concentrations of luteinizing hormone therein, the sample indicating the maximum concentration of luteinizing hormone in said body fluid being that of the day of ovulation of the woman.

4. The method of claim 1 wherein said predetermined amount of anti-human chorionic gonadotropin is selected as the amount which will react with the equivalent of up to 50 international units per liter of chorinic gonadotropin.

5. The method of claim 3 wherein said predetermined amount of anti-human chorionic gonadotropin is selected as the amount which will react with luteinizing hormone in an amount which is the equivalent of up to 50 international units of human chorionic gonadotropin per liter of body fluid.

6. The method of claim 3 wherein the test sensitivity is increased by diluting the urine.

* * * * *